United States Patent [19]

Heil, Jr. et al.

[11] Patent Number: 4,819,661

[45] Date of Patent: Apr. 11, 1989

[54] POSITIVE FIXATION CARDIAC ELECTRODE WITH DRUG ELUTION CAPABILITIES

[75] Inventors: Ronald W. Heil, Jr., Roseville; Robert C. Owens, Forest Lake, both of Minn.

[73] Assignee: Cardiac Pacemakers, Inc., St. Paul, Minn.

[21] Appl. No.: 112,519

[22] Filed: Oct. 26, 1987

[51] Int. Cl.⁴ ............................................... A61N 1/00
[52] U.S. Cl. .................................... 128/786; 128/639
[58] Field of Search ............. 128/639, 642, 783, 784, 128/785, 786

[56] References Cited

U.S. PATENT DOCUMENTS

| | | | |
|---|---|---|---|
| 3,737,579 | 6/1973 | Bolduc | 128/785 |
| 3,788,329 | 1/1974 | Friedman | 128/786 |
| 4,058,116 | 11/1977 | Bucalo | 128/642 |
| 4,146,036 | 3/1979 | Dutcher et al. | 128/785 |
| 4,282,885 | 8/1981 | Bisping | 128/785 |
| 4,378,023 | 3/1983 | Trabucco | 128/785 |
| 4,408,604 | 1/1983 | Hirshorn et al. | 128/785/ |
| 4,577,642 | 3/1986 | Stokes | 128/784 |
| 4,601,294 | 7/1986 | Danby et al. | 128/642 |
| 4,679,572 | 7/1987 | Baker, Jr. | 128/786 |
| 4,711,251 | 12/1987 | Stokes | 128/784 |

FOREIGN PATENT DOCUMENTS 47013 of 0000 European Pat. Off. .

Primary Examiner—Francis Jaworski
Assistant Examiner—George Manuel
Attorney, Agent, or Firm—Orrin M. Haugen; Thomas J. Nikolai; Frederick W. Niebuhr

[57] ABSTRACT

A positive fixation cardiac lead includes an electrode sleeve/crimp tube assembly in which a recess is formed for retaining a drug impregnated matrix. The electrode sleeve and crimp tube threadedly engage, to permit insertion of the matrix prior to their assembly. The distal end section of the crimp tube can be provided with a helical groove corresponding to the shape of a fixation helix, with the sleeve and distal section spaced from one another to permit insertion of an annular drug matrix. The distal portion of the electrode sleeve can have an annular groove formed to receive a length of platinum wire, for increased electrode sensitivity.

15 Claims, 1 Drawing Sheet

U.S. Patent Apr. 11, 1989 4,819,661
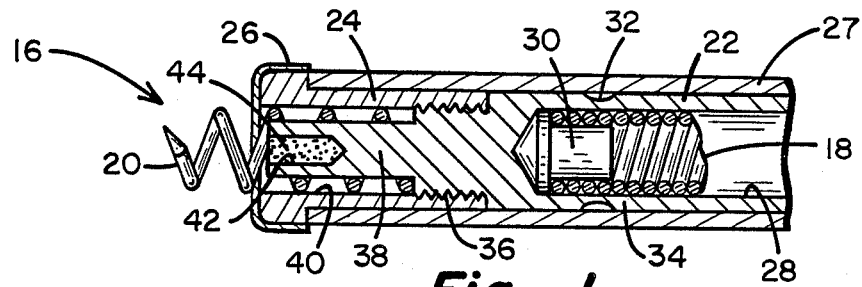
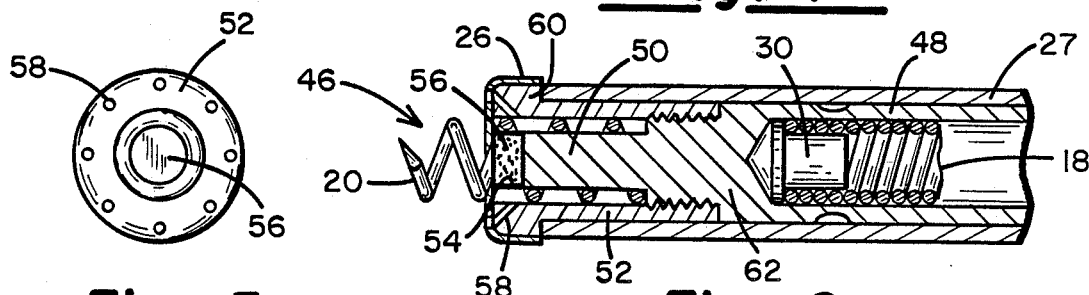
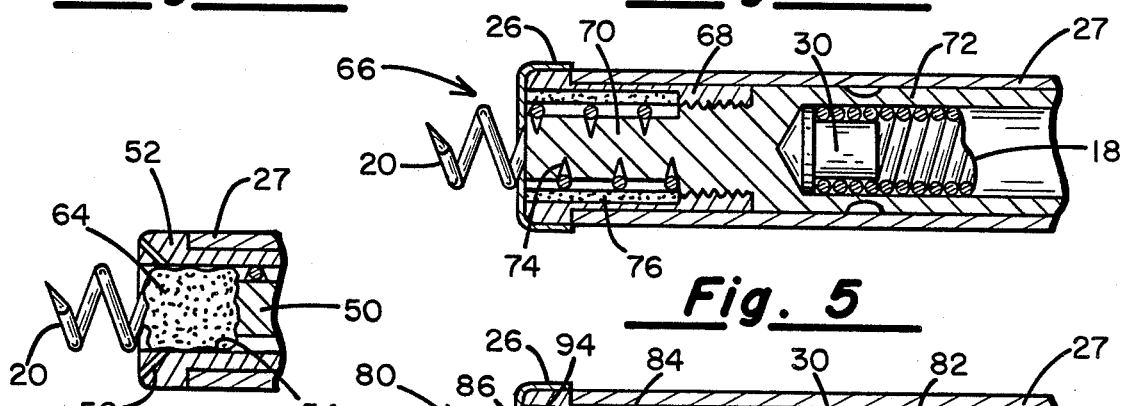
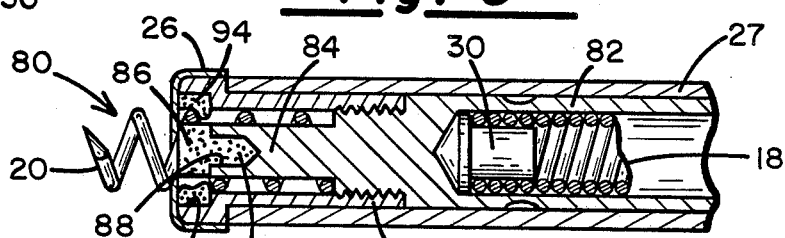
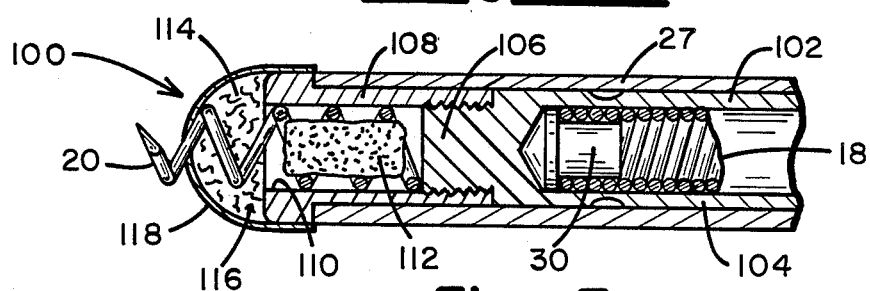

POSITIVE FIXATION CARDIAC ELECTRODE WITH DRUG ELUTION CAPABILITIES

BACKGROUND OF THE INVENTION

This invention relates to cardiac diagnostic and chronic therapeutic leads, and more particularly to fixation leads having an anchoring element and capable of delivering drugs near the point of fixation.

Cardiac pacing leads are well known as a means for carrying pulse stimulation signals from pacing devices to the heart, and for monitoring heart electrical activity from outside the body. Typically, such leads are sufficiently flexible and small in diameter to allow intravenous introduction into a cardiac cavity, whereupon an electrode at the distal end of the lead is implanted into the endocardium to secure the lead. For this purpose, helical coils, barbs or other tissue piercing fixation elements often are provided, typically as part of or integral with the electrode.

The anchoring or fixation element must be sufficiently sharp to pierce and penetrate the endocardium and secure the electrode against becoming detached, for example due to contractions of the myocardium. During a critical period immediately after implant and prior to full fibrotic growth, usually three to twelve weeks, the anchoring element must provide substantially the entire force maintaining the electrode in its chosen location. Moreover, the interaction between the electrode and body tissue at the point of implant gives rise to both acute and chronic increases in the stimulation threshold. Consequently, pacing devices must be designed to deliver pulses of sufficient amplitude to exceed the increased threshold, or an attempt is made to minimize the increase.

One technique for reducing stimulation thresholds is the elution of a drug in the area of implant. For example, U.S. Pat. No. 4,577,642 (Stokes) discloses a drug dispensing body implantable lead in which an electrode member 16 includes a recess for housing a molecular sieve material which retains a drug, alternatively a solid plug or a powder. The electrode tip provides a sintered elution path which regulates the dispensing of the drug to counteract the chronic increase in stimulation threshold. Another approach to increasing lead sensitivity and attempting to minimize the increase in stimulation threshold is to provide a porous electrode tip. For example, U.S. Pat. No. 4,408,604 (Hirshorn et al) discloses a pacemaker electrode tip, with apertures 19 through the tip. These apertures are said to improve attachment of the electrode to surrounding tissue, as well as to reduce the sensing impedance of the tip.

These prior art approaches, while suitable for certain applications, fail to address the need for rapid drug delivery to counter acute threshold increase, and for the positive fixation of a lead distal tip in combination with drug elution near the tip to reduce both acute and chronic stimulation threshold.

Therefore, it is an object of the present invention to provide a positive fixation cardiac pacing lead adapted for rapid drug delivery immediately upon implant to counter an acute stimulation threshold increase.

Another object is to provide a positive fixation cardiac pacing lead having a porous electrode for local delivery of a therapeutic drug upon implant, in combination with a drug impregnated matrix for chronic drug delivery.

Another object of the invention is to provide a positive fixation cardiac pacing lead containing a drug impregnated matrix for chronic drug delivery, and having an electrode tip particularly configured for increased sensitivity to cardiac electrical activity.

Yet another object is to provide a positive fixation cardiac pacing lead constructed for convenient, proximal end loading of a drug delivery matrix into the coupling structure between the lead electrode and distal end of a lead conductor.

SUMMARY OF THE INVENTION

To achieve these and other objects, there is provided an intravascular lead implantable inside a patient, including an elongate and flexible electrical conductor. The lead further includes a distal end assembly including an electrode, a fixation element fixed with respect to the electrode for effecting penetration into endocardial tissue at a selected location to secure the electrode at the selected location, and a coupling means for electrically and mechanically joining the electrode and a distal end of the conductor. A flexible, biocompatible and dielectric sheath surrounds the conductor along substantially the entire length thereof, and also surrounds the assembly along at least a proximal end region thereof. A chamber in the assembly is open to its distal end, and a matrix impregnated with a therapeutic drug is retained in the chamber.

The chamber may be formed directly in the coupling means and open to the coupling means distal end. Alternatively, the electrode can include a tubular sleeve which extends beyond the distal end of the coupling means to define the chamber. Or, the electrode sleeve can be mounted in surrounding, spaced apart relation to a generally cylindrical distal end portion of the coupling means, and thus define an annular chamber. This latter arrangement permits the use of an annular drug delivery matrix, resulting in a greater surface area for a given size matrix and therefore more rapid drug delivery.

The electrode is preferably porous. In one embodiment, a series of apertures is provided in the distal end region of the electrode sleeve, open to the chamber and to the electrode exterior. Alternatively, an annular recess is formed in the electrode sleeve distal end, and platinum wire is embedded in the recess in order to increase the surface area of the electrode tip. Yet another approach utilizes fine platinum wire, stretched, then packed against the distal end of the electrode sleeve, and retained against the sleeve by a screen overlying the platinum wire and attached to the sleeve. The packed wire electrode is highly porous and can be preloaded with a therapeutic drug in liquid or solid form, for rapid delivery at the location of implant. The apertures, when provided in the electrode sleeve, can be similarly pre-loaded.

Thus, in accordance with the present invention there is provided a positive fixation lead particularly well adapted for countering the acute increase in stimulation threshold immediately after implant, as well as reducing the chronic threshold stimulation level.

IN THE DRAWINGS

For a better appreciation of these and other features and advantages, reference is made to the following detailed description of the invention, along with the drawings, in which:

FIG. 1 is a side sectional view of the distal end region of an implantable, positive fixation, cardiac lead constructed in accordance with the present invention;

FIG. 2 is a side sectional view of the distal end region of a second embodiment cardiac lead;

FIG. 3 is an end elevation of an electrode sleeve of the cardiac lead of FIG. 2, with parts removed to enhance illustration of certain features;

FIG. 4 is an enlarged partial side elevation of the cardiac lead of FIG. 2, illustrating an alternative drug delivery matrix;

FIG. 5 is a side sectional view of the distal end region of a third embodiment cardiac lead;

FIG. 6 is a side sectional view of the distal end region of a fourth embodiment cardiac lead; and FIG. 7 is a side sectional view of the distal end region of a fifth embodiment cardiac lead.

DETAILED DESCRIPTION OF THE PREFERRED EMBODIMENTS

Turning now to the drawings, there is shown in FIG. 1 the distal end region of an implantable, positive fixation, cardiac pacing lead 16. Devices such as lead 16 typically are inserted intravenously, for example into the subclavian vein or cephalic vein, and moved progressively toward the heart until the distal end reaches a selected cardiac chamber. With the distal tip positioned at a selected location, the lead proximal end, still outside the body, is maneuvered to implant the distal tip into the endocardium. The implanted lead transmits electrical signals between the selected location in the heart and the lead proximal end, for one or both of two purposes: to monitor heart electrical activity at the selected location, and to carry pulse stimulation signals to the selected location from a pulse generator (not shown) connected to the lead proximal end.

To transmit the electrical signals there is provided an electrical conductor, shown in FIG. 1 as a double-wound coil 18 formed of a nickel alloy. The coil provides maximum flexibility for conforming to the vein, with minimal stress on the conductor. At the distal end of the lead is an integral assembly including an electrode, a fixation helix 20, and a crimp tube 22, all preferably constructed of a platinum alloy. Helix 20 typically is spot welded to the crimp tube. The electrode includes an elongate, annular electrode sleeve 24 somewhat enlarged at its distal end, and a porous screen 26 overlying the sleeve distal end and fixed to the sleeve. A flexible, dielectric sheath 27 surrounds coil conductor 18 and electrode sleeve 24 over the majority of its length. The sheath is formed of a biocompatible material such as silicone rubber. Screen 26 can be arranged in two layers if desired, and aids in chronic lead fixation, as fibrous connective tissue intertwines with the screen to firmly secure the electrode.

Fibrous encapsulation, however, can take weeks, and it is therefore advantageous to provide fixation helix 20 as a means for positively securing the lead distal end during the time immediately following implantation. To this end, helix 20 has a sharp distal point which readily penetrates the endocardium. Upon such penetration, the helix is manipulated from the proximal end of lead 16, whereby it rotates clockwise to further penetrate the tissue, to the point of firmly securing electrode sleeve 24 and screen 26 at the designated endocardial location.

Crimp tube 22 is provided for electrically and mechanically coupling electrode sleeve 24 and the distal end of conductor 18. More particularly, the conductor distal end is secured in a proximal recess 28 of the crimp tube by a core pin 30 and a crimp 32 formed in the tube near the core pin. The crimp tube has a stepped configuration, with a relatively large diameter proximal end section 34 about proximal recess 28, a reduced diameter medial section 36 which preferably has external threads for a threaded engagement with electrode sleeve 24, and a further reduced diameter distal end section 38. Distal section 38 and sleeve 24 are thus spaced apart from one another and define an annular recess 40 which accommodates the proximal portion of fixation helix 20 for a fixed mounting to distal end section 38. Crimp tube 32 includes a distal chamber 42 open to the distal end of the crimp tube. Contained in chamber 42 is a drug loaded matrix 44, preferably a biocompatible silicone adhesive compound, and impregnated with dexamethasone sodium phosphate or other desired therapeutic drug. Screen 26 retains matrix 44 in chamber 42.

In use, lead 16 is inserted and implanted in myocardial tissue as previously described. Immediately upon implant, bodily fluid in the vicinity of the selected myocardial location enters chamber 42 through screen 26, resulting in the elution of the therapeutic drug from matrix 44 into the body. The matrix may tend to swell upon its exposure to bodily fluids. To accommodate this swelling, screen 26 can be spaced apart from the distal faces of matrix 44 and crimp tube 22 as shown. The eluting drug counteracts the stimulation threshold increase, thereby permitting stimulation pulses of a lower amplitude, thus to increase the useful life of the pacing apparatus at the proximal end of conductor 18.

A second embodiment cardiac lead 46 is illustrated in FIG. 2. Lead 46 is substantially identical to lead 16 in many respects, and like parts are given like numerals. A crimp tube 48 of lead 46 differs from crimp tube 22 in that no distal chamber is formed therein. Rather, the length of a distal section 50 of crimp tube 48 is reduced, whereby an electrode sleeve 52 extends distally beyond the distal section. Consequently, in addition to the annular spacing between distal section 50 and electrode sleeve 52 for accommodating fixation helix 20, there is provided a generally cylindrical chamber 54 for containment of a cylindrical or disk-shaped matrix 56, which is impregnated with a therapeutic drug.

The porosity of screen 26 permits drug elution from the generally cylindrical chamber 54 to the region about the distal face of lead 46. To further enhance elution, a series of apertures 58 are formed in a distal portion 60 of electrode sleeve 52, arranged symmetrically about the distal face of the electrode sleeve as seen in FIG. 3. Helix 20 and screen 26 are removed to enhance illustration of the apertures. Apertures 58 facilitate flow of bodily fluids between the chamber and lead exterior, thus facilitating elution.

In the case of leads 16 and 46, each respective drug impregnated matrix can be preformed, and loaded into its respective recess prior to the assembly of the respective crimp tube and electrode sleeve. To this end, medial sections 36 and 62 can be provided with external threads, with sleeves 24 and 52 provided with corresponding internal threads for a threaded engagement. While a threaded engagement is preferred, an adhesive could be employed as an alternative connecting means.

FIG. 4 shows an alternative arrangement utilizing second embodiment lead 46, which permits assembly of the lead prior to injection of the drug impregnated matrix. In particular, a drug impregnated matrix 64 (in lieu of disk-shaped matrix 56) is loaded into chamber 54 through one or more of apertures 58, while matrix 64 is in a viscous or malleable state. Matrix 64 cures and solidifies subsequent to loading. If desired, apertures 58 as well can be loaded with matrix 64.

FIG. 5 illustrates the distal portion of a third embodiment cardiac lead 66, similar to the previously discussed leads in certain respects whereby like parts are assigned like numerals. An electrode sleeve 68 of the lead includes an internal, annular recess extending from the sleeve distal end along the entire length of a distal section 70 of a crimp tube 72, thus to provide a wider annular gap between distal section 70 and sleeve 68. A groove 74 is formed in distal crimp tube section 70, having a helical shape conforming to the configuration of fixation helix 20, to permit a threaded engagement of the helix and crimp tube for a more positive helix/crimp tube connection.

The combined effect of the sleeve recess and helical groove 74 is to provide a gap of sufficient size for insertion of an annular drug impregnated matrix 76. Annular matrix 76, as compared with matrices 56 and 44, has a substantially greater ratio of surface area to volume, and thus permits a more rapid drug elution.

A fourth embodiment cardiac lead 80 is shown in FIG. 6. A crimp tube 82 has a distal section 84 which is somewhat shortened to accommodate a preformed cylindrical first drug impregnated matrix 86. Further, a chamber 88 is provided in distal section 84 to accommodate a second drug carrying matrix 90. An internal recess 91 is formed in the distal end region of an electrode sleeve 92, effectively enlarging the distal inside diameter of the electrode sleeve. A fine platinum wire 94 is mounted into recess 91, to provide an increased electrode surface area to enhance fibrous encapsulation. Further, wire 94 functions as an antenna, to substantially enhance sensitivity of lead 80.

FIG. 7 shows the distal end region of a fifth embodiment cardiac lead 100. A crimp tube 102 includes a proximal section 104 and distal section 106 provided with external threads for engagement with internal threads of an electrode sleeve 108. Crimp tube 102 thus lacks the reduced diameter distal end portions of previously discussed embodiments, and sleeve 108 and distal section 106 define a relatively large cylindrical chamber 110 which accommodates fixation helix 20 and a relatively large cylindrical, preformed drug impregnated matrix 112. An advantage of this configuration is that it permits proximal end loading of matrix 112 into chamber 110 prior to engagement of the electrode sleeve and crimp tube.

An electrode tip 114, including stretched, crimped and tightly packed fine wire 116, retains matrix 112 within chamber 110, and in turn is contained against the distal face of electrode sleeve 108 by a generally hemispherical screen 118 fastened to the distal end portion of the sleeve. Electrode tip 114 is constructed of a platinum alloy, stretched to a thin wire or line, then packed against the distal end of electrode sleeve 108. So constructed, the electrode tip is highly porous, for example consisting of approximately twenty percent platinum alloy by volume, with the remaining eighty percent open to receive a therapeutic drug in liquid form or solid form, or to permit passage of bodily fluids through the electrode tip between chamber 110 and the lead exterior.

A substantial treatment advantage is provided by lead 100, in that electrode tip 114 may be loaded with a therapeutic drug particularly suited for rapid delivery at the site of implant, while matrix 112 can be loaded with a drug more suitable for chronic treatment. The acute and chronic stimulation threshold increases are then treated separately. Also, the platinum wire in tip 114 acts as an antenna, to enhance lead sensitivity.

Thus, in accordance with the present invention a positive fixation cardiac pacing lead can be adapted for rapid delivery of a therapeutic drug immediately upon implant to counter an acute stimulation threshold increase. Moreover, the immediate drug delivery means may be combined with a matrix suited to chronic drug delivery. If desired, the sensitivity of the lead to pulses can be enhanced by provision of the above-described annular recess at the distal end of the electrode sleeve, and mounting a platinum wire within the recess. Also, in accordance with the present invention the electrode sleeve and crimp tube are configured for threaded engagement after insertion of a preformed drug impregnated matrix into a chamber at the distal end of the electrode/crimp tube assembly, providing a convenient alternative to injection of the matrix.

What is claimed is:

1. An intravascular lead implantable inside a patient, including:
   an elongate and flexible electrical conductor;
   a lead distal end assembly including an electrode, a fixation element fixed with respect to said electrode for effecting penetration into endocardial tissue at a selected location to secure said electrode at said selected location, and a coupling means for electrically and mechanically joining said electrode and a distal end section of said conductor, wherein said electrode includes an elongate annular sleeve and a porous electrode tip at a distal end of the sleeve, said porous electrode tip comprising an electrically conductive fine wire crimped and packed adjacent said distal end of the sleeve, and a screen overlying said wire and fastened to the sleeve to secure said wire relative to the sleeve;
   a flexible, biocompatible and dielectric sheath surrounding said conductor along substantially the entire length thereof, and surrounding said assembly along at least a proximal end region thereof;
   means forming a chamber in said assembly and open to a distal end thereof; and
   a matrix impregnated with a therapeutic drug and retained in said chamber.

2. The intravascular catheter of claim 1 wherein:
   said chamber is cylindrical, and is formed in said coupling means and open to a distal end thereof.

3. The intravascular catheter of claim 1 wherein:
   said electrode includes an elongate sleeve mounted in spaced apart, surrounding relation to a distal end section of said coupling means, thereby to locate said chamber between said elongate sleeve and said distal end section of the coupling means, and wherein the shape of said matrix corresponds to the shape of said chamber.

4. The intravascular catheter of claim 3 wherein:
   said distal end section of the coupling means is cylindrical, and said elongate sleeve is radially spaced apart from said distal end section, thereby to define said chamber as annular.

5. The intravascular lead of claim 4 wherein:
   said fixation element comprises a helical coil, and wherein means form a helical groove along said distal end section of said coupling means corresponding to said helical coil, for securing a portion of said helical coil within said groove and threadedly to said coupling means.

6. The intravascular catheter of claim 1 wherein:
said electrode includes an elongate sleeve surrounding a distal end section of said coupling means, and a distal end portion of the sleeve extends beyond the distal end section of the coupling means to define said chamber adjacent said distal end section.

7. The intravascular catheter of claim 6 wherein:
said distal end section of the coupling means is generally cylindrical, and said elongate sleeve is annular, thereby to define said chamber as generally cylindrical.

8. The intravascular lead of claim 6 further including:
means forming a plurality of apertures in a distal end portion of the sleeve open to said chamber and to the exterior of said sleeve at locations distal with respect to said sheath.

9. The intravascular lead of claim 1 wherein:
said electrode includes an elongate, annular sleeve, means defining an annular recess in a distal end of said sleeve, and an electrically conductive fine wire embedded in said recess.

10. The intravascular lead of claim 1 wherein:
said fixation element comprises a helical coil, and wherein means form a helical groove along a distal end section of the coupling means corresponding to said helical coil, for securing a portion of said helical coil within said groove and threadedly to said coupling means.

11. The intravascular, implantable lead comprising:
an elongate and flexible electrical conductor;
a lead distal end assembly including an electrode sleeve, a fixation element fixed with respect to the electrode sleeve for effecting penetration into endocardial tissue at a selected location to secure said electrode sleeve at said selected location, and a coupling means for electrically and mechanically joining said electrode sleeve and a distal end of said conductor;
a flexible, biocompatible and dielectric sheath surrounding said conductor along substantially the entire length thereof, and surrounding said assembly along at least a proximal end region thereof;
means forming a chamber in said electrode sleeve, and a matrix impregnated with a therapeutic drug, said chamber being open to a proximal end of said electrode sleeve to permit proximal insertion of said matrix into said chamber;
wherein a distal end section of said coupling means is adapted to engage the proximal end of said electrode sleeve, following said proximal insertion of said matrix, to retain said matrix in said chamber and to form a substantially fluid tight seal between said matrix and said conductor; and
means forming a fluid passageway for movement of body fluid into and out of said chamber distally with respect to said coupling means.

12. The intravascular, implantable lead of claim 11 wherein:
said electrode sleeve and said distal end section threadedly engage.

13. The intravascular, implantable lead of claim 11 further including:
a porous electrode tip at a distal end of said electrode sleeve, said tip comprising an electrically conductive fine wire crimped and packed adjacent said distal end, and a screen overlying said wire and fastened to the sleeve to secure said wire relative to the sleeve.

14. An intravascular lead implantable inside a patient, including:
an elongate and flexible electrical conductor;
a lead distal end assembly including an electrode, a helical coil for effecting penetration into endocardial tissue at a selected location to secure said electrode at said selected location, and a coupling means for electrically and mechanically joining said electrode and a distal end section of said conductor; and
means forming a helical groove along a distal end section of said coupling means and corresponding to said helical coil, said helical coil including a proximal portion surrounding said distal end section of said coupling means and lying within said groove, whereby said proximal portion of said helical coil is within said groove and thereby threadedly secured to said coupling means.

15. An intravascular lead implantable inside a patient, including:
an elongate and flexible electrical conductor;
a lead distal end assembly including an electrode, a helical coil for effecting penetration into endocardial tissue at a selected location to positively secure said electrode at said selected location, and a coupling means for electrically and mechanically joining said electrode and a distal end section of said conductor, said electrode including an elongate annular sleeve and an electrode tip at a distal end of said sleeve, said electrode tip having a porosity of at least 75%;
a flexible, biocompatible and dielectric sheath surrounding said conductor along substantially the entire length thereof, and surrounding said assembly along at least a proximal end region thereof;
means forming a chamber in said assembly and open to a distal end thereof; and
a solid matrix impregnated with a therapeutic drug and retained in said chamber.

* * * * *